United States Patent
Maetzler et al.

(10) Patent No.: US 10,248,373 B2
(45) Date of Patent: Apr. 2, 2019

(54) ANALYSIS SYSTEM FOR ANALYZING BIOLOGICAL SAMPLES, DATA PROCESSING METHOD AND COMPUTER PROGRAM PRODUCT

(71) Applicant: Roche Diagnostics Operations, Inc., Indianapolis, IN (US)

(72) Inventors: Marco Maetzler, Rotkreuz (CH); Juergen Wiemer, Oberaegeri (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 190 days.

(21) Appl. No.: 15/018,006

(22) Filed: Feb. 8, 2016

(65) Prior Publication Data
US 2016/0154621 A1    Jun. 2, 2016

Related U.S. Application Data

(63) Continuation of application No. 12/774,144, filed on May 5, 2010, now abandoned.

(30) Foreign Application Priority Data

May 6, 2009   (EP) .................................... 09159499

(51) Int. Cl.
*G06F 3/14*      (2006.01)
*G06F 19/26*     (2011.01)
(Continued)

(52) U.S. Cl.
CPC ........ *G06F 3/1454* (2013.01); *G06F 3/04842* (2013.01); *G06F 3/04845* (2013.01); *G06F 19/28* (2013.01); *G06F 19/26* (2013.01)

(58) Field of Classification Search
CPC .............. G06F 3/1454; G06F 3/04842; G06F 3/04845; G06F 19/28
(Continued)

(56) References Cited

U.S. PATENT DOCUMENTS 6,710,790 B1 *    3/2004   Fagioli .................. G06F 3/0481
                                                        715/778
2002/0062068 A1 *  5/2002   Gritzbach .............. G06Q 50/22
                                                        600/300
(Continued)

FOREIGN PATENT DOCUMENTS

DE         100 57 781 A1   11/2000
EP         0487383 A2       5/1992
(Continued)

*Primary Examiner* — Angie M Badawi
(74) *Attorney, Agent, or Firm* — Dinsmore & Shohl, LLP

(57) ABSTRACT

Embodiments related to analysis system for analyzing biological samples, a data processing method and a computer program product are disclosed. An analyzer is coupled to an control computer and has a control application program which receives control data, sends analytical data, and generates a host screen image. A remote computer is coupled to the control computer, and provides a data manager application program which sends the control data to the control computer, receives the analytical data, and generates a first window. A remote application program interoperates with a host application program which generates a second window containing a duplicate of the host screen image. A user interface program displays a first display window and a second display window, the first display window being one of the first and second windows and the second display window containing a screen shot of the other one of the first and second windows.

19 Claims, 10 Drawing Sheets

(51) Int. Cl.
*G06F 19/28* (2011.01)
*G06F 3/0484* (2013.01)

(58) Field of Classification Search
USPC .......................................................... 715/733
See application file for complete search history.

(56) References Cited

U.S. PATENT DOCUMENTS

| | | | |
|---|---|---|---|
| 2005/0073503 A1 | 4/2005 | Fudali et al. | |
| 2006/0069764 A1 | 3/2006 | Azuma et al. | |
| 2006/0253791 A1* | 11/2006 | Kuiken | G06F 3/0481 |
| | | | 715/766 |
| 2007/0020764 A1* | 1/2007 | Miller | G01N 35/0092 |
| | | | 436/45 |
| 2007/0180140 A1 | 8/2007 | Welch et al. | |
| 2008/0028314 A1 | 1/2008 | Bono et al. | |
| 2008/0034104 A1 | 2/2008 | Kariti et al. | |
| 2008/0058963 A1 | 3/2008 | Garibaldi et al. | |
| 2008/0168850 A1 | 7/2008 | Fischer | |
| 2008/0288830 A1 | 11/2008 | Marinucci | |
| 2009/0307600 A1* | 12/2009 | Arthur | G06F 3/1454 |
| | | | 715/740 |
| 2010/0001876 A1* | 1/2010 | Sasaki | G01N 35/00732 |
| | | | 436/56 |

FOREIGN PATENT DOCUMENTS

| | | |
|---|---|---|
| EP | 1107159 A2 | 6/2001 |
| EP | 1 818 812 A1 | 1/2006 |
| EP | 1 862 928 A1 | 12/2007 |
| EP | 1 959 257 A2 | 2/2008 |
| JP | 2002517814 A | 6/2002 |
| JP | 2003279583 A | 10/2003 |
| JP | 2004054783 A | 2/2004 |
| JP | 2005129068 A | 5/2005 |
| JP | 2006108947 | 4/2006 |
| JP | 2006338672 | 12/2006 |
| JP | 2007192840 A | 8/2007 |
| JP | 2007521522 A | 8/2007 |
| JP | 2008118317 | 5/2008 |
| JP | 2008203004 A | 9/2008 |
| JP | 2009005367 | 1/2009 |
| JP | 2009505300 A | 2/2009 |
| JP | 2009522663 A | 6/2009 |
| JP | 2009539078 A | 11/2009 |
| WO | 98/26365 | 6/1998 |
| WO | 99/10801 | 3/1999 |
| WO | 2007/137751 A1 | 12/2007 |

* cited by examiner

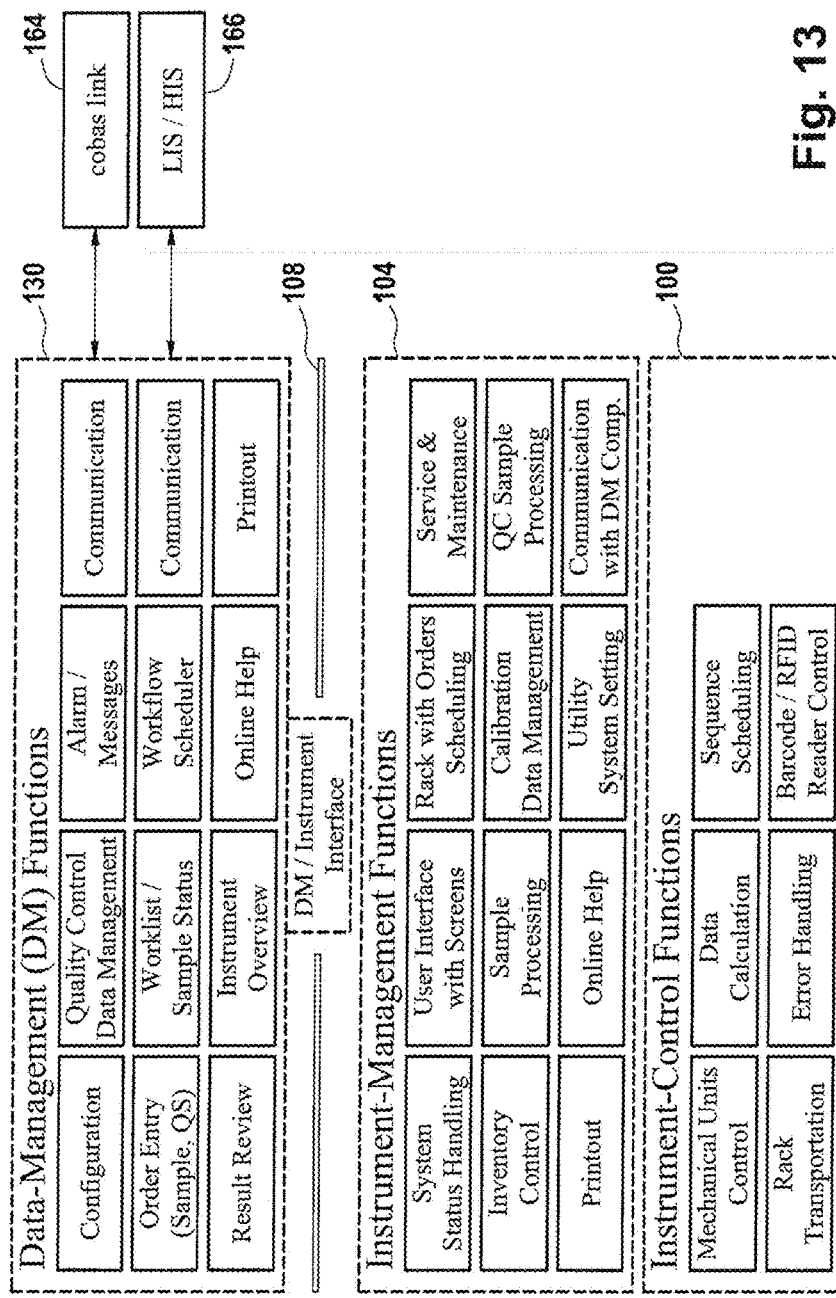

ANALYSIS SYSTEM FOR ANALYZING BIOLOGICAL SAMPLES, DATA PROCESSING METHOD AND COMPUTER PROGRAM PRODUCT

CROSS-REFERENCE TO RELATED APPLICATIONS

The present application is filed under 35 U.S.C. § 111 as a continuation of U.S. application Ser. No. 12/774,144, filed on May 5, 2010, which claims priority to European Application No. 09159499.4, filed on May 6, 2009, the contents of which are hereby incorporated by reference in their entirety.

TECHNICAL FIELD

Embodiments of the present invention relate generally to the field of analysis system, and in particular, various embodiments relate to an analysis system for analyzing biological samples, such as body fluids, a data processing method, and a computer program product.

BACKGROUND

Various automatic analyzers are known for analyzing biological samples such as analyzers for in-vitro analysis of biological samples. EP1 959257 A2 shows an example of such an automatic analyzer.

US 2008/0168850 A1 shows a display for simultaneously monitoring analytical devices. The display has a primary section that shows device information for each analytical device in the device group. The device information has a plurality of information fields.

SUMMARY

In one embodiment, an analysis system for analyzing biological samples is disclosed and comprises at least one analyzer coupled to a respective analyzer control computer. The analyzer control computer comprises an analyzer control application program which receives control data and sends analytical data, the analyzer control application program generates a host screen image, and further comprising a host application program. The at least one analyzer operates to induce a reaction of a biological sample with a reagent and to acquire at least one measurement value being related to the reaction. A remote computer is coupled to the at least one analyzer control computer. The remote computer comprises a data manager application program which sends the control data to the at least one analyzer control computer and receives the analytical data, the data manager application program generates a first window, and further comprising at least one remote application program. The remote application program interoperates with the host application program to generate a second window containing a duplicate of the host screen image. A user interface program is provided which displays at least a first display window and a second display window, the first display window being one of the first and second windows and the second display window containing a screen shot of the other one of the first and second windows, wherein only the first display window permits entry of user data. An input unit is provided to enter a user's selection of the first or the second window for displaying as the first display window.

In another embodiment, a data processing method implemented by a remote computer and a number N of n analyzer control computers is disclosed. The method comprises: generating a host screen image by each one of the analyzer control computers; generating the number N of windows by the remote computer, the nth window being a duplicate of the nth host screen image; and displaying a first display window and the number N of second display windows, the first display window being one of the windows and each one of the N second display windows containing a screen shot one of the windows, wherein each one of the analyzer control computers is coupled to an analyzer and wherein user interaction with one of the analyzer control computers is enabled via the first display window.

In still another embodiment, a computer program product is disclosed which comprises executable program code which causes a remote computer and a number N of n analyzer control computers to perform at least the above mentioned method embodiment of the invention.

Other and further features and advantages of these and other embodiments of the invention will appear more fully from the following detailed description and the accompanying drawings.

BRIEF DESCRIPTION OF THE DRAWINGS

FIG. 13 depicts a block diagram showing a further embodiment of an analysis system of the invention.

LIST OF REFERENCE NUMERALS

Figure 1:
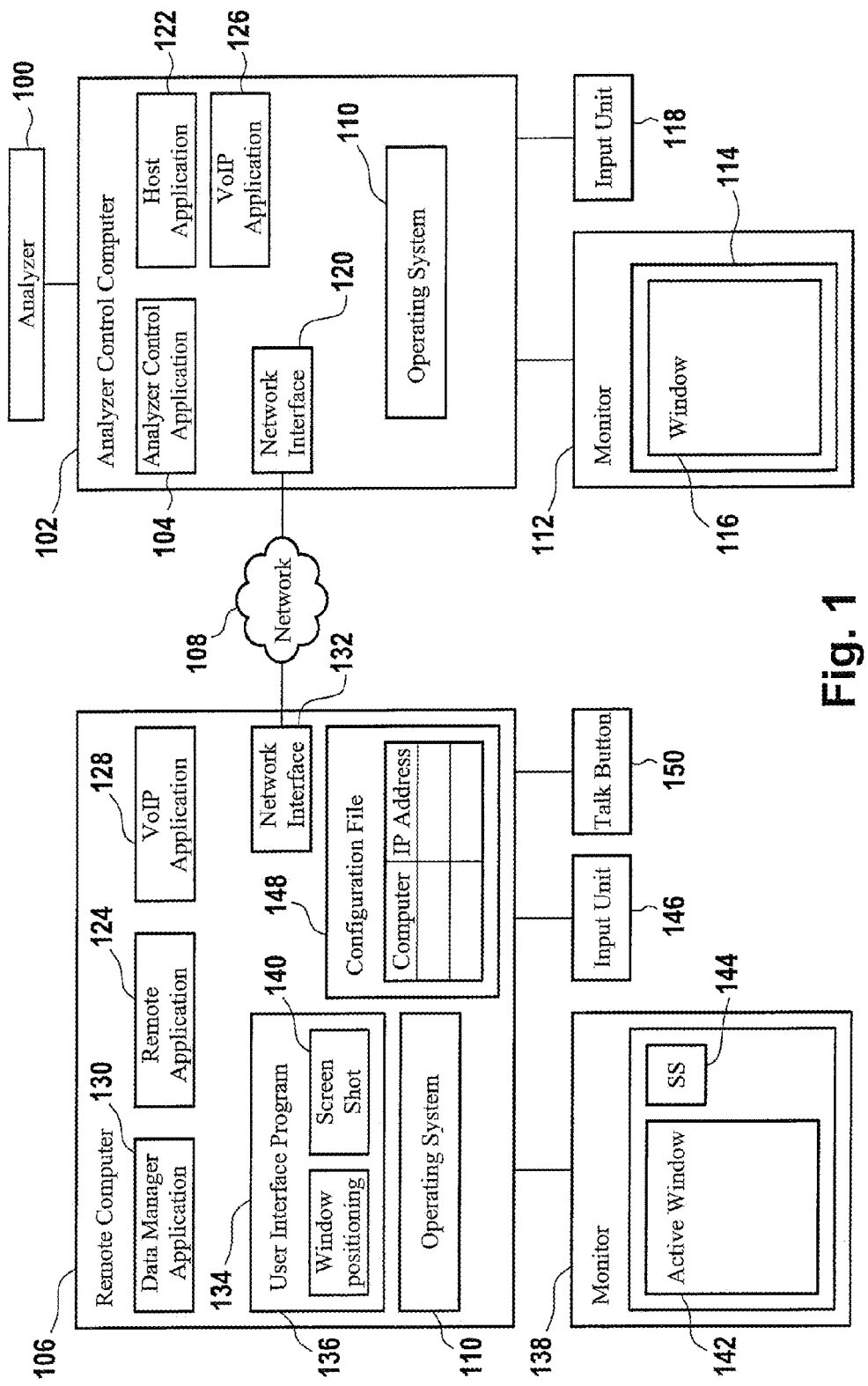
FIG. 1 depicts a block diagram of an embodiment of an analysis system of the invention.

100 Automatic analyzer
102 Analyzer control computer
104 Analyzer control application program
106 Remote computer
108 Network
110 Operating system
112 Monitor
114 Host screen image
116 Window
118 Input unit
120 Network interface
122 Host application program 124 Remote application program
126 VOIP application program
128 VOIP application program
130 Data manager application program
132 Network interface
134 User interface program
136 Window positioning component
138 Monitor
140 Screen shot component
142 Active window
144 Window
146 Input unit
148 Configuration file
150 Button
152 Side bar
154 Stack
156 Cursor
158 Screen
160 Data entry fields
162 screen image
164 External computer
166 external computer

DETAILED DESCRIPTION

In accordance with various embodiments on the invention, an analysis system for analyzing biological samples is provided that comprises at least one automatic analyzer. The automatic analyzer is adapted to analyze a biological sample, such as a body fluid. The automatic analyzer is coupled to an analyzer control computer that serves as a control unit for the automatic analyzer. The analyzer control computer executes an analyzer control application program for receiving control data from a remote computer and for sending analytical data to the remote computer.

The term 'control data' as used herein encompasses any kind of data for specifying or enabling a requested action of the automatic analyzer, including data specifying the biological sample to be analyzed, e.g. by an identifier such as an order number, and optionally the kind of analysis to be performed on the biological sample.

The term 'analytical data' as used herein encompasses any data that is descriptive of a result of an analysis performed by the automatic analyzer and an identifier of the biological sample that has been analyzed, in particular the so called order number. In case of a calibration the analytical data comprises the calibration result, i.e. calibration data. In particular, the analytical data comprises an identifier of the sample for which the analysis has been performed and data being descriptive of a result of the analysis, such as measurement data.

The analytical data in one embodiment comprises result context data. The term 'result context data' encompasses any data that is descriptive of the conditions under which the measurement data has been obtained, e.g. the reagents that have been used for performing the analysis, any problems that may have occurred during the performance of the analysis, calibration settings of the analyzer at the time of performing the analysis, demographic data of the patent who's sample has been analyzes and/or other data related to the context of the analysis. The usage of context data is further described in WO 2007/137751 A1.

The term "analyzer" as used herein encompasses any apparatus that can induce a reaction of a sample with a reagent for obtaining a measurement value. The reaction is induced by the analyzer in accordance with control data that specifies one or more parameters related to the reaction. The measurement value can be provided as part of the analytical data. The kind of measurement value that is acquired by the analyzer depends on the specified reaction. For example, the analyzer measures light absorption, fluorescence, electrical potential or other physical or chemical characteristics of the reaction to provide the measurement data.

The analyzer control application is adapted to generate a host screen image. Depending on the implementation the host screen image may enable an operator's direct interaction with the analyzer control application program via an input unit of the analyzer control computer. Alternatively, no monitor is coupled to the analyzer control computer such that the host screen image is not displayed at the location of the analyzer control computer. It is important to note that even when no monitor is coupled to the analyzer control computer the host screen image is still generated by the analyzer control application. The analyzer control computer further comprises a host application program.

In accordance with some embodiments of the invention, the analyzer control computer does not have a monitor coupled to it and/or it does not have an input unit coupled to it such that a user interaction with the analyzer control computer is only possible from a remote computer.

The analyzer control computer is coupled to the remote computer. The remote computer comprises a data manager application program for sending the control data to the analyzer control computer and for receiving the analytical data from the analyzer control computer. The data manager application program is operable to generate a first window for a user's interaction with the data manager application program using the remote computer. The remote computer further comprises at least one remote application program that is adapted to interoperate with the host application program of the analyzer control computer for generating a second window containing a duplicate of the host screen image.

Hence, the interoperation of the remote application program and the respective host application program enables to remotely control the analyzer control computer using the second window when the second window is displayed by the remote computer. Such remote and host application programs are as such known from prior art, for example from U.S. Pat. No. 6,710,790. In particular, the PCAnywhere™ software from Symantec Corporation (Mountain View, Calif.), can also be used to implement the host and remote application programs. For the purpose of the screen duplication of the host screen image on the remote computer each one the analyzer control computers constitutes a host computer running a copy of the host application program.

The remote computer further comprises a user interface program for displaying at least a first display window and a second display window. The first display window constitutes the active window into which the user can enter data. The first display window is one of the first and second windows. In other words, the first display window is either the first window of the data manager application program or the second window that contains the duplicate of the host screen image.

The second display window that is displayed by the user interface program is a screen shot of at least another window that is not shown in the first display window. For example, when the first window of the data manager application program is displayed as the first display window, the second display window shows a screen shot of the second window that contains the duplicate of the host screen image. In addition, a further second display window can be shown that contains a screen shot of the window that is displayed as the first display window. Further, additional second display windows can be shown for additional analyzer control computers.

A 'screen shot' as understood herein encompasses an image taken by the remote computer of one of the first and second windows. For example, the screen shot has a bitmap image format, such as BMP, PNG or JPEG. It is to be noted that the term 'screen shot' as used herein does not necessarily imply that an image of the full screen is taken but rather an image of just a portion of the screen, such as an individual window.

In accordance with various embodiments of the invention, the first window that is generated by the data manager application program and/or the second window that is generated by the remote application program of the remote computer is not necessarily visible on a monitor that is coupled to the remote computer. What is displayed on the monitor of the remote computer are at least the first display window and the second display window.

The first window that is generated by the data manager application program is selected by the user interface program to be displayed as the first display window upon a user's selection of the first window to become the active window into which the user can enter data. Likewise, the second window that is generated by the remote application program is selected by the user interface program to be displayed as the first display window upon a user's selection of the second window to become the active window into which the user can enter data.

In accordance with another embodiment of the invention, the second display window contains a screenshot of the second window that is generated by the remote application program if the user has selected the first window generated by the data manager application program to be the active window that is displayed as the first display window. In this instance the second window is not displayed on the monitor but only the screenshot of the second image by means of the second display window. In this situation the user cannot enter data into the second window as only a screenshot of the second window is shown by the second display window on the monitor but not the second window itself. When the user wants to enter data into the second window the user has to enter a selection of the second window, such as by clicking on its screenshot, in order to select the second window to become the active window, i.e. the first display window.

The remote computer further comprises input means that enable a user to enter a selection of the window that is to be displayed as the first display window. The input means can be realized by any type of computer peripheral input device, such as by a keyboard, computer mouse, trackball, a pen entry device, by voice control or the like.

For example, a user can click on the second display window in order to select the screen whose screen shot is shown in the second display window for displaying as the first display window. This implies that the window that is currently displayed as the first display window is deselected. The selection of the window can be performed by moving a pointer such as a mouse cursor, onto the second display window and then entering a selection command, such as by clicking on a mouse button.

Although not limited thereto, various embodiments of the invention are particularly advantageous as the user's interaction with the at least one automatic analyzer is greatly facilitated. In particular, the user can remotely monitor and control the automatic analyzer using the remote computer without having to be physically present at the analyzer control computer's location.

Furthermore, various embodiments of the invention are also particularly advantageous as the user can only enter data into the first display window but not into the second display window as the second display window does only contain a screen shot. This ensures that the user cannot inadvertently or accidentally enter data into the second window which could cause a malfunction of the automatic analyzer or loss of an important biological sample. In particular, the user cannot inadvertently enter data into the window whose screen shot is shown by the second display window when the second display window is selected such as by a mouse click on the second display window.

In accordance with an embodiment of the invention, the user interface program of the remote computer is adapted to repeatedly update the screen shot. This has the advantage of enabling monitoring of the host screen image and thus of the status of the automatic analyzer.

In accordance with an embodiment of the invention, a time interval between two consecutive screen shot updates is below five seconds, and in another embodiment below one second.

In accordance with an embodiment of the invention, the data manager application program transforms the analytical data and result context data into human readable analytical re-sults. In particular, this encompasses an aggregation and/or validation of the data received by the data manager application program from the analyzer control computer.

In accordance with an embodiment of the invention, the same physical network, such as an Ethernet, is utilized for transmission of the analytical data, the control data and/or for the data transmission between the remote application program and the host application program. Separate interfaces can be implemented on logical layers of the network transmission protocol for transmission of the various kinds of data. For example, the HL7 interface is used for transmission of a sample identifier and a request to perform a certain analysis on the sample identified by the sample identifier from the data manager application program to the analyzer control computer of the analyzer that is to perform the requested analysis. The HL7 interface is also used for transmission of at least a portion of the analytical data that contains a description of a result of the analysis together with the sample identifier from the analyzer control computer back to the data manager application program in response to the request.

In addition, an XML interface may be utilized for exchanging data between the data manager application program and the analyzer control computer via the network. For example, at least a portion of the control data that specifies the analysis to be performed can be transmitted from the data manager application program to the analyzer control computer by means of an XML document containing control data. Likewise, at least a portion of the analytical data, such as result context data, is communicated back from the analyzer control computer to the data manager application program as an XML document containing the result context data.

The communication between the remote application program and the host application program may also be performed via the same physical network using still another logical interface, such as the proprietary PCAnywhere protocol.

In accordance with an embodiment of the invention a user's selection of one of the second windows to become the active window implies that data entry into the respective analyzer control computer is only enabled via the active window shown on the monitor of the remote computer.

When one of the selected second windows becomes the active window no data entry is possible into the original window displayed on the monitor coupled to the analyzer control computer of which the selected second window contains a duplicate.

In accordance with an embodiment of the invention, a plurality of automatic analyzers is coupled to a single remote computer through their respective analyzer control computers. Each one of the analyzer control computers runs an instance of the host application program and the remote computer runs an instance of the remote application program for each one of the analyzer control computers to provide a second window for each one of the analyzer control computers.

In the following the number of analyzer control computers is designated by N, where N can be any integer number that is greater or equal to one. The nth analyzer control computer of the plurality of analyzer control computers is coupled to the nth automatic analyzer and the analyzer control application program of the nth analyzer control computer generates an nth host screen image, where $0<n<N+1$ and where n is an integer number. By interoperation of the nth host application program with the nth remote application program of the remote computer the nth second window containing a duplicate of the nth host screen image is generated by the remote computer.

In accordance with an embodiment of the invention the analysis system comprises a number N of the automatic analyzers, an nth automatic analyzer being coupled to an nth analyzer control computer, the analyzer control application program of the nth analyzer control computer being adapted to generate an nth host screen image and the nth analyzer control computer comprising an nth host application program, wherein the remote computer comprises the number N of the remote application programs for generating an nth second window for the nth analyzer control computer, the nth second window containing a duplicate of the nth host screen image, the first display window being one of the first and N second windows and the second display window being another one of the first and N second windows.

In accordance with an embodiment of the invention the user can select the first window or one of the N second windows for display as the first display window via the input means. For each of the second windows and for the first window there is a second display window containing a screen shot of the respective window. This enables a user to conveniently and instantaneously select one of the second windows or the first window to become the window that is displayed in the first display window, such as for entering data into that window. Hence, the total number of second display windows is N+1 in the embodiment considered here.

In accordance with an embodiment of the invention, the user interface program has a window positioning component for stacking the first window and the N second windows on top of each other such that a user interaction is only enabled with the topmost window of the stack. In other words, only the topmost window of the stack is visible as it is an overlay covering all the other windows of the stack such that a user can only enter data into the topmost window of the stack. For example, the first window and the second windows have identical size and format.

All of these windows are stacked on top of each other and are vertically aligned. As a consequence the topmost window completely covers all the other windows of the stack such that only the topmost window is accessible for performing data entry. The topmost window of the stack thus constitutes the first display window.

In accordance with an embodiment of the invention, the order of the stack is changed in response to the user's selection of another window to become the first display window. This is particularly advantageous as the selected window is immediately moved to the top of the stack in order to become visible to the user and in order to enable data entry of the user into that window with a minimal latency time. This is due to the fact that the up-to-date window the user has selected is already present in the stack and does not need to be generated or updated when the user enters his or her selection. This is particularly advantageous to provide real time capability with limited latency times which can be useful if rapid user interaction with one of the automatic analyzers becomes necessary such as in the case of a malfunctioning or another critical state of the automatic analyzer.

In accordance with an embodiment of the invention, the remote computer and the analyzer control computers have means for establishing a voice communication channel. This enables to establish a voice communication channel between the remote computer and any one of the analyzer control computers. This is particularly advantageous as it enables the user of the remote computer to communicate with another user of one of the automatic analyzers such as to instruct the user of the automatic analyzer to manually perform a certain maintenance operation or the like.

In accordance with an embodiment of the invention, the remote computer and the at least one analyzer control computer comprise voice communication means for establishing a voice communication channel between the remote computer and the at least one analyzer control computer for voice communication between the user of the remote computer and a user of the at least one analyzer control computer.

In accordance with an embodiment of the invention, the remote computer further comprises means for receiving a single user entry action, wherein the means for establishing the voice communication channel are adapted to establish the voice communication channel between the remote computer and one of the analyzer control computers whose second window is displayed as the first display window in response to the single user entry action.

In accordance with an embodiment of the invention, the remote computer has means for receiving a user entry action. When the means for receiving a user entry action is operated by the user the voice communication channel is established between the remote computer and the analyzer control computer whose host screen image is currently shown in the first display window. This is particularly advantageous as the user of the remote computer can enter into voice communication with the relevant user of the automatic analyzer by performing a single entry action, such as by pushing a talk button or by clicking on a virtual button that is displayed on the user interface.

In another embodiment, a data processing method is implemented by a remote computer and a number N of analyzer control computers.

In still another embodiment, a computer program product, such as a digital storage medium, comprising computer executable instructions for performing an embodiment of the data processing method of the invention is disclosed.

Illustrative embodiments of the invention are explained hereafter in greater detail by way of example only and by making reference to the drawings in which like numbered elements in these figures are either identical elements or perform the same function. As such, elements which have been discussed previously will not necessarily be discussed in later figures if the function is identical.

FIG. 1 shows an analysis system for analyzing biological samples comprising at least one automatic analyzer 100 for analyzing the biological samples. For example, the automatic analyzer 100 is operable to perform in-vitro analysis of a body fluid of a patient, such as a blood or urine analysis.

The automatic analyzer 100 is coupled to a analyzer control computer 102. The analyzer control computer 102 executes an analyzer control application program 104. The analyzer control application program 104 receives control data from a remote computer 106 via a network 108. The network 108 can operate in accordance with the internet protocol (IP). For example, the network 108 can be implemented as an Ethernet.

When the analyzer control application program 104 receives a request containing control data from the remote computer 106 it generates one or more commands for the automatic analyzer 100 for execution of the request. The analyzer 100 responds to the commands by sending analytical data back to the analyzer control application program 104 whereby the analytical data can be descriptive of a result of the analysis performed on one of the biological samples. The analyzer control application program 104 sends a response back to the remote computer 106 via the network 108 whereby the response contains the analytical data received from the analyzer 100.

The analyzer control application 104 generates a host screen image that is rendered under the control of an operating system 110 of the analyzer control computer 102 on a monitor 112 that may be coupled to the analyzer control computer 102.

The operating system 110 provides a graphical user interface including windows. For example, the operating system 110 can be a Microsoft operating system, such as Microsoft Windows, in one embodiment or an Apple Macintosh operating system in another embodiment.

The host screen image 114 that is displayed by the monitor 112 includes a window 116 that is generated by the analyzer control application program 104. The window 116 may include up to date status information of the automatic analyzer and one or more data entry fields for entry of control data by a user, i.e. a human operator. The data entry can be performed by means of an input unit 118 that may be coupled to the analyzer control computer 102, such as a keyboard and/or a computer mouse.

The analyzer control computer 102 has a network interface 120 for coupling the analyzer control computer 102 to the network 108. Further, the analyzer control computer 102 runs a host application program 122 that interoperates with a respective remote application program 124 that is executed by the remote computer 106.

The analyzer control computer 102 is loaded with a voiceover IP (VoIP) program 126 that interoperates with a respective VoIP program 128 that is executed by the remote computer 106.

The remote computer 106 can have the same or a different operating system 110 as the analyzer control computer 102 that also includes a graphical user interface providing windows. The remote computer 106 executes a data manager application program 130 for sending the control data via a network interface 132 over the network 108 to the analyzer control application program 104 of the analyzer control computer 102 and for receiving analytical data from the analyzer control application program 104 in response to a request containing the control data.

Further, the remote computer 106 executes a user interface program 134 that comprises a window positioning component 136 for positioning windows on a monitor 138 that is coupled to the remote computer 106. The user interface program 134 further comprises a screen shot component 140 for taking screen shots. The user interface program 134 controls the operating system 110 such that an active window 142 and at least one additional window 144 containing a screen shot (SS) is displayed on the monitor 138.

The active window 142 may have one or more data entry fields into which the user can enter data such as by means of an input unit 146 that is coupled to the remote computer 106. The input unit 146 can be a keyboard and/or a computer mouse or another computer peripheral.

The window 144 has the purpose of displaying a screen shot and does not allow entry of any data by the user.

The data manager application program 130 generates a first window and the remote application program 124 generates a second window containing a duplicate of the host screen image 114 while it interacts with the host application program 122.

The active window 142 is either the first window or the second window whereas the window 144 contains a screen shot of the first window or the second window depending on the user's selection received via the input unit 146.

The remote computer 106 stores a configuration file 148 that specifies the IP addresses of the one or more analyzer control computers that are coupled to the remote computer 106. In the embodiment considered here the IP address of the analyzer control computer 102 is entered into the configuration file 148 in order to enable IP communication between the remote computer 106 and the analyzer control computer 102 via the network 108.

A button 150 is coupled to the remote computer 106. When the user of the remote computer 106 presses the button 150 the VoIP application program 128 is invoked and a voice communication channel is established via the network 108 whereby the VOIP application program 128 interoperates with the VOIP application program 126.

In the following it is assumed without restriction of generality that the first window that is generated by the data manager application program 130 is positioned by the window positioning component 136 as the active window 142 whereas the second window that is generated by the remote application program 124 is shown as a screen shot provided by the screen shot component 140 in the window 144. In one embodiment, the active window 142 is much larger than the window 144 and covers at least 50% of the display area of the monitor 138.

Via the input unit 146 the user can select the second window to be displayed as the active window such as by performing a mouse click on the window 144. In response the window positioning component 136 positions the second window on the monitor 138 to become the active window 142 and the screen shot component 140 provides a screen shot of the first window which is then shown as the window 144.

Hence, when the second window becomes the active window 142 the first window is shown as a screen shot in window 144. Alternatively it is also possible that a separate screen shot for each of the first and second windows is permanently shown on the monitor 138.

For example, the user selects the first window generated by the data manager application program 130 to become the first display window, i.e. the active window 142. The second window that is generated by the remote application program 124 is shown as a screenshot in the second display window, i.e. window 144. The second window generated by the remote application program 124 itself is however not shown on the monitor 138.

The user may enter data into the active window 142, i.e. the first window generated by the data manager application program 130, for specifying a request for the performance of the analysis of a sample by the analyzer 100. The data manager application program 130 sends a respective request including a sample identifier via the network 108 to the analyzer control computer 102 for processing by the analyzer control application program 104 upon the user's entry of the data into the active window 142. It is important to note that the transmission of the request including the sample identifier is performed via the network 108 without involving the host application program 122.

The remote computer 106 and the analyzer control computer 102 may implement a first interface for the transmission of the request including the sample identifier from the remote computer 106 to the analyzer control computer 102 and/or for the transmission of the respective result data including the sample identifier from the analyzer control computer 102 to the remote computer 106. For example, the first interface is the HL7 interface as standardized by Health Level 7, Inc. In addition or alternatively the remote computer 106 and the analyzer control computer 102 implement a second interface, such as an XML interface, for transmission of at least a portion of the control data and/or the analytical data, in particular the result context data.

For directly communicating with the analyzer control application program 104 without going through the intermediary of the data manager application program 130 the user selects the second window generated by the remote application program 124 to become the active window 142. In response, the second window that contains a duplicate of the host screen image 114 including the window 116 that is generated by the analyzer control application program 104 is shown as the active window 142. The user may enter data into the active window 142 that is now the duplicate of the host screen image 114 via the input unit 146. The data entered by the user into the active window 142 is transformed into image data by the remote application program 124 and communicated as image data to the host application program 122 which then enters this data into the analyzer control application program 104.

The transmission of data between the remote computer 106 and the analyzer control computer 102 can be performed using the same physical layer provided by the network 108 irrespective of the fact whether the data is transmitted through the intermediary of the data manager application program 130 or not.

Figure 2:
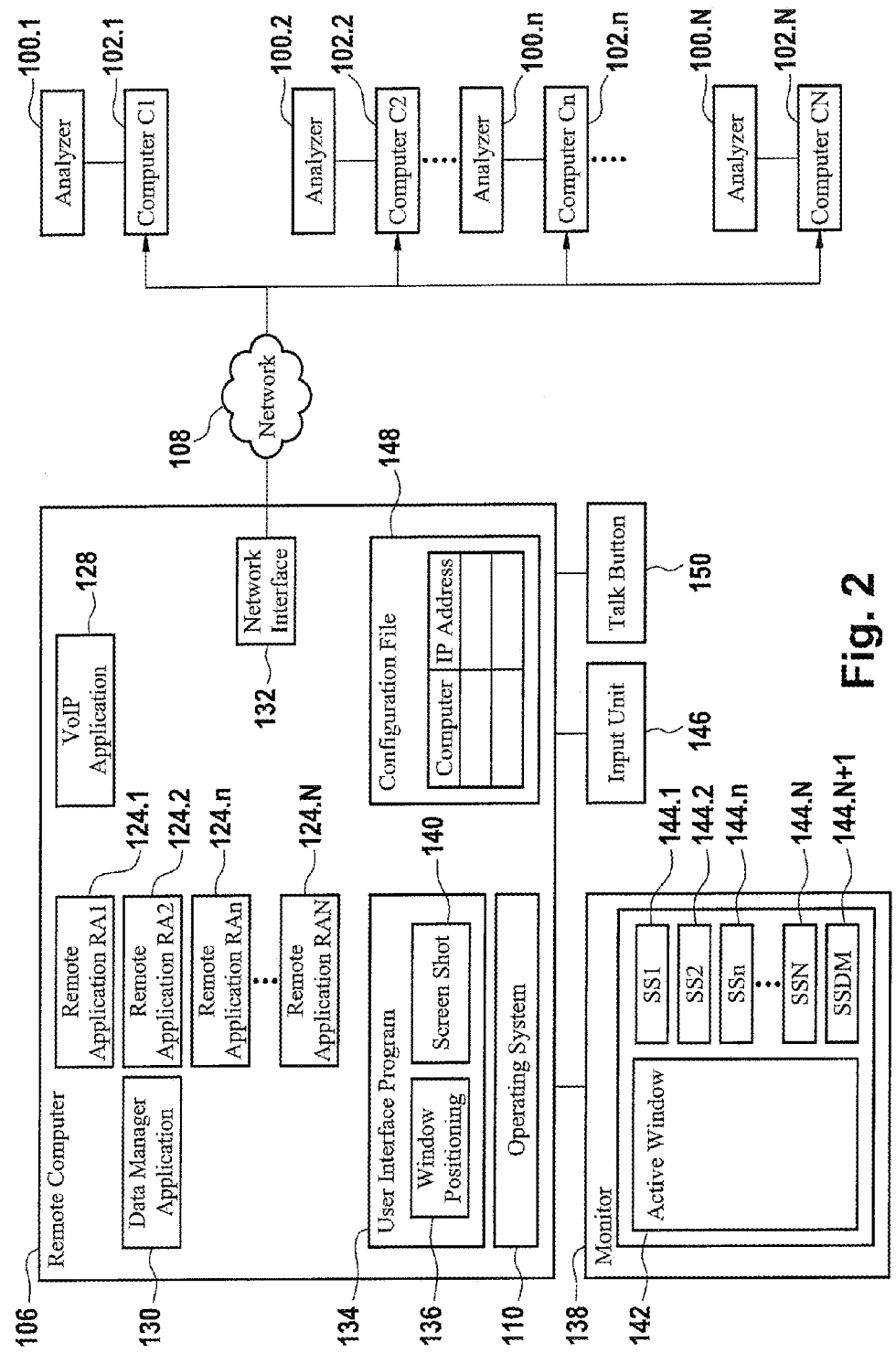
FIG. 2 depicts a block diagram of a further embodiment of an analysis system of the invention.

FIG. 2 shows an embodiment of the analysis system where a number of N analyzers 100.1, 100.2, . . . , 100.*n*, . . . , 100.N are coupled to the remote computer 106 via the network 108 through their respective analyzer control computers, i.e. analyzer control computer C1 102.1, analyzer control computer C2 102.2, . . . , analyzer control computer Cn 102.*n*, . . . , analyzer control computer CN 102.N.

The automatic analyzers 100.1 to 100.N can be designed to perform various kinds of analysis of biological samples. The analyzer control computers C1 to CN have the same or similar functionalities as the analyzer control computer 102 shown in FIG. 1. In particular, each one of the analyzer control computers Cn locally runs an instance of the host application program 122.

The remote computer 106 runs an instance of the remote application program 124 for each one of the N analyzer control computers Cn. In other words, the remote computer 106 executes a remote application (RA) program RA1 124.1 for the analyzer control computer C1, a remote application program RA2 124.2 for the analyzer control computer C2, . . . , a remote application program RAn for the analyzer control computer Cn, . . . , and remote application program RAN 124.N for analyzer control computer CN.

Each one of the remote application programs RAn generates a second window that contains a duplicate of the host screen image of the analyzer control computer Cn to which it is assigned. Hence, the remote application programs RAn generate a number of N second windows.

The screen shot component 140 provides screen shots for each of the N second windows which are displayed as windows 144.1 to 144.N on the monitor 138. In other words, the window 144.1 that is displayed on the monitor 138 contains the screen shot SS1 of the 1th second window generated by the remote application program RA1, the window 144.2 contains the screen shot SS2 of the 2th second window provided by the remote application program RA2, . . . , the window 144.*n* contains the screen shot SSn of the nth second window provided by the remote application RAn, . . . , and the window 144.N contains the Nth second window provided by the remote application program RAn.

In addition, the screen shot component also provides a screen shot SSDM of the first window generated by the data manager application program 130 which is shown as window 144.N+1 on the monitor 138.

One of the N second windows 144.*n* or the first window is displayed on the monitor 138 as the active window 142 into which the user can enter data. Without restriction of generality it is assumed here that the first window provided by the data manager application program 130 is initially shown as the active window 142. The user of the remote computer 106 can thus conveniently interact with the data manager application program 130 while monitoring the N analyzers 100.1 to 100.N. If direct interaction with one of the analyzers 100.*n* becomes necessary as indicated to the user on the respective window 144.*n*, the user can enter a selection of the respective nth second window via the input unit 146 such as by performing a mouse click on the window 144.*n*. In response the nth second window becomes the active window 142. The windows 144.1 to 144.N+1 are updated repeatedly but remain unchanged otherwise by the user's selection of the active window 142.

When the user of the remote computer 106 needs to talk to an operator of the analyzer control computer Cn while the nth second window is displayed as the active window 142, the user of the remote computer 106 does only need to perform a single input action such as by pressing the button 150 as this invokes the VoIP application program 128 that establishes a voice-over-IP voice communication channel to the analyzer control computer Cn using the IP address of the analyzer control computer Cn given in the configuration file 148. Hence, the user of the remote computer 106 can immediately talk to the operator of the analyzer control computer Cn such as for providing emergency instructions or explanations on how to properly operate or maintain the analyzer 100.*n*.

Figure 3:
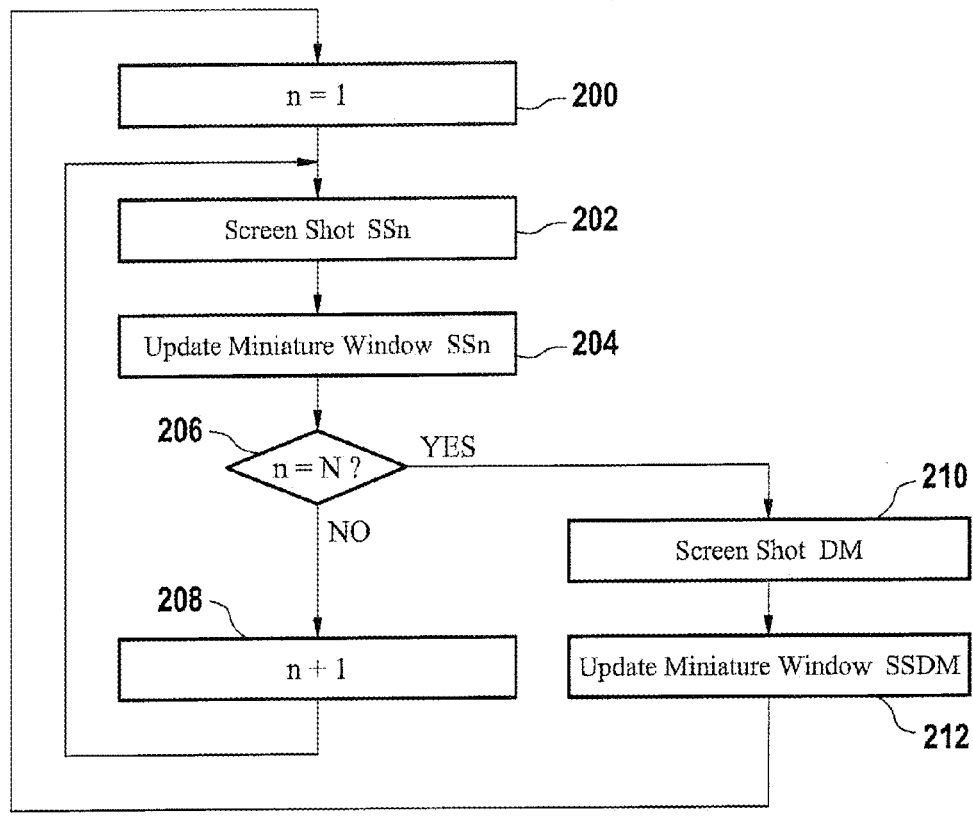
FIG. 3 depicts a flowchart illustrating an embodiment of a method of the invention.

FIG. 3 is a flow diagram which illustrates the updating of the screen shots shown in the windows 144.1 to 144.N+1 in the embodiment of FIG. 2.

In step 200 the index n is initially set to 1. In step 202 the screen shot SSn of the nth second window is taken and the miniature window 144.*n* is updated with that new screen shot SSn in step 204.

In step 206 it is decided whether n=N. If this is not the case, n is incremented in step 208 and the control returns to step 202. If n=N then the control goes from step 206 to step 210 where a screen shot SSDM of the first window provided by the data manager application program is taken. In the following step 212 the respective miniature window 144.N+1 is updated with that new screen shot SSDM and the control goes back to step 200.

The process shown in FIG. 3 can be implemented by the screen shot component 140 in the embodiments of FIGS. 1 and 2. The speed of execution of the process shown in FIG. 3 can be chosen such that the update frequency of each of the miniature windows 144.n is below two seconds in one embodiment, and below one second in another embodiment.

Figure 4:
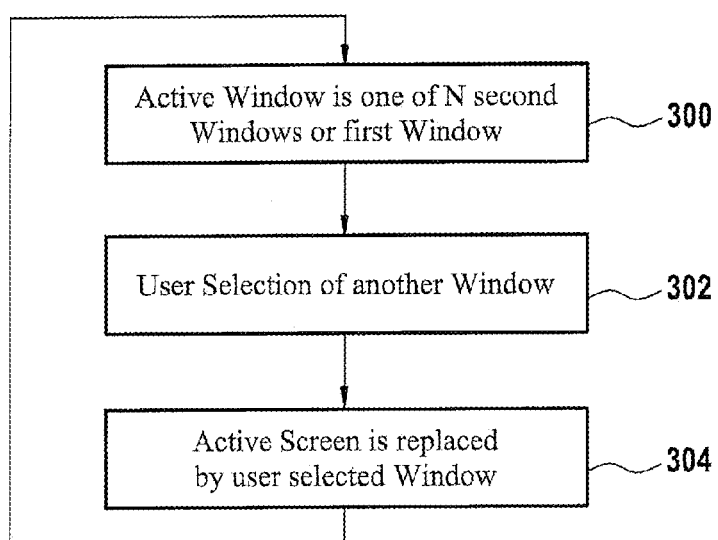
FIG. 4 depicts a flowchart illustrating a further embodiment of a method of the invention.

FIG. 4 is a flowchart illustrating another process that can be executed concurrently with the updating process that permanently runs in the background. In step 300 the active window that is displayed on the monitor of the remote computer is one of the N second windows or the first window. In step 302 a user selects another one of the N second windows or the first window to become the new active window such as by performing a mouse click on the respective miniature window that shows the screen shot of the window that is to become the new active window. In step 304 the window the user has selected in step 302 becomes the new active window replacing the active window of step 300. From step 304 the control goes back to step 300 for a consecutive user's selection of another one of the windows to become the new active window.

Figure 5:
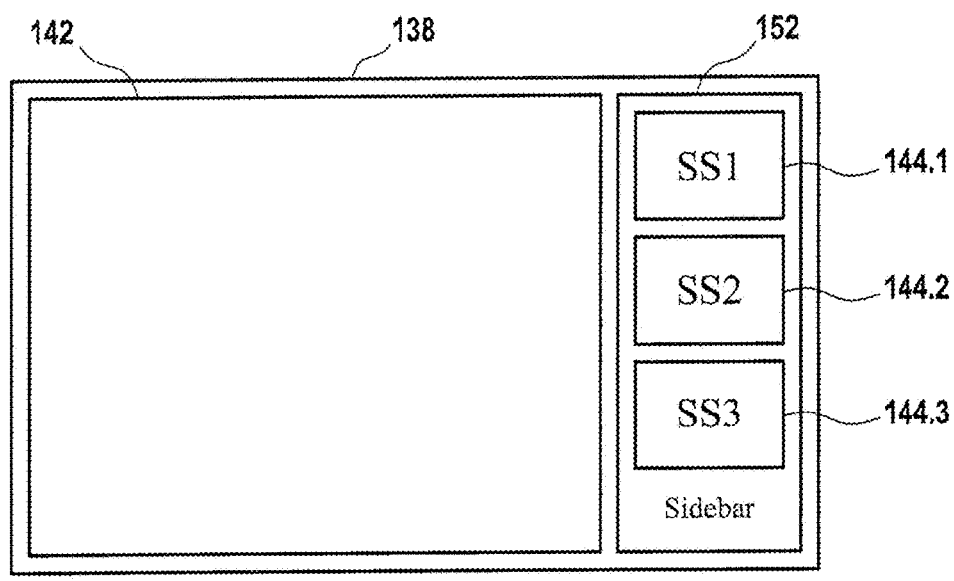
FIG. 5 depicts an embodiment of a screen image displayed on the remote computer in accordance with an embodiment of the invention.

FIG. 5 shows an embodiment where the windows 144.1 to 144.3 are arranged in a side bar 152. FIG. 5 shows a status of the analysis system where the second window provided by remote application program RA1 is shown as the active window 142. The windows 144.1 to 144.3 may or may not contain a window showing the screen shot SSDM.

Figure 6:
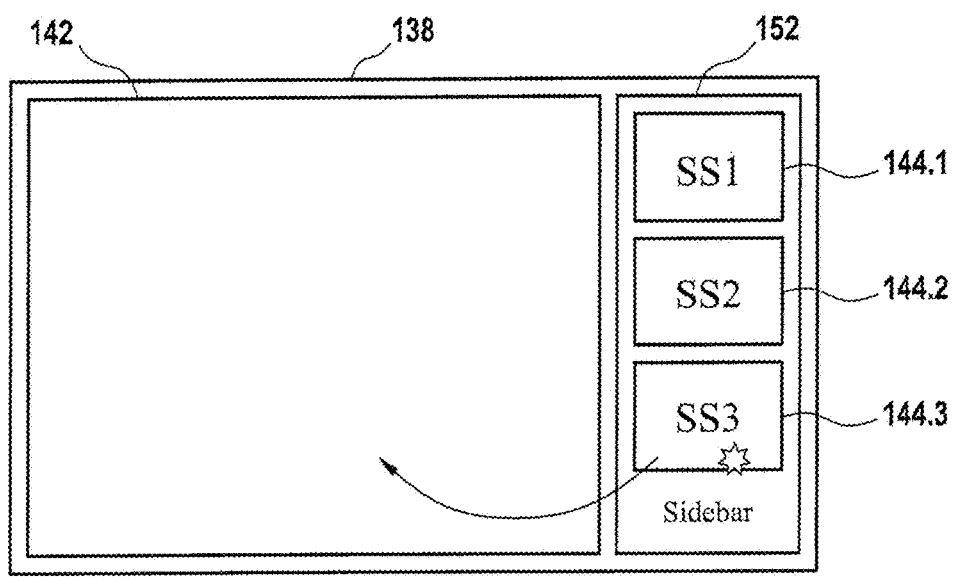
FIG. 6 depicts the screen image of FIG. 5 when the user selects another window.

FIG. 6 is illustrative of the process for replacing the active window 142 by another one of the windows upon a user's selection. When the user clicks on the miniature window 144.3 as indicated by the star in FIG. 6 the current active window is replaced by the window whose screen shot is shown in the window 144.3.

Figure 7:
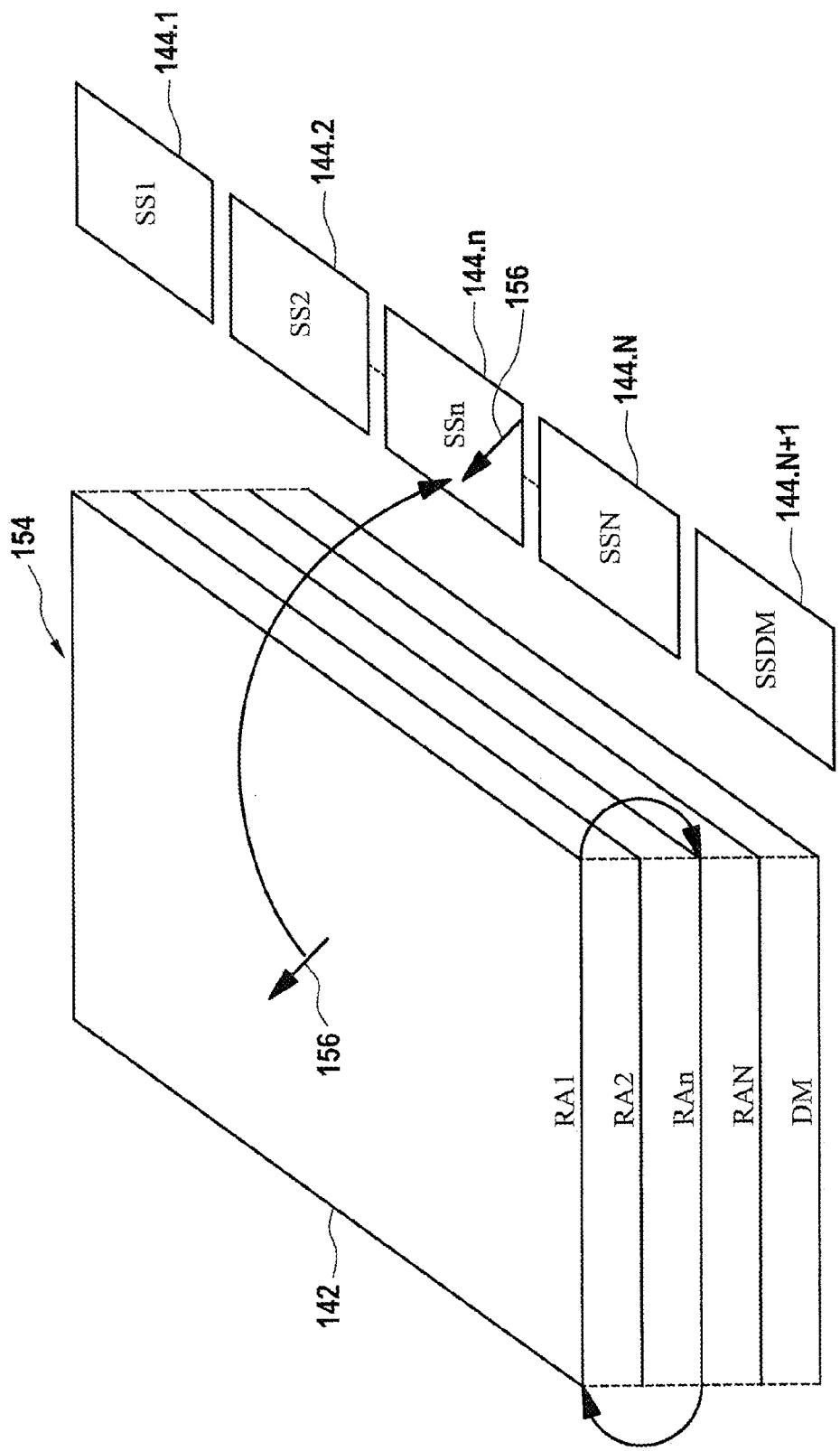
FIG. 7 depicts a schematic view illustrating the positioning of the windows on the screen of the remote computer in accordance with an embodiment of the invention.

FIG. 7 illustrates an embodiment of the positioning of the various windows that is performed by an embodiment of the window positioning component 136 of the remote computer 106 (cf. FIGS. 1 and 2).

In the embodiment considered here the first window generated by the data manager application program 130 and all N second windows 144.n that are generated by the remote application programs RAn are positioned to form a stack 154 such that the active window 142 is the topmost window of the stack and is completely covering all the other windows of the stack 154 such that only the topmost active window 142 is visible. As the topmost active window 142 of the stack 154 is providing an overlay for all the other windows of the stack 154 a user can only access that active window 142 such as for entry of data. However, the user cannot move a cursor 156 onto one of the windows that are positioned below the topmost active window 142 of the stack 154.

FIG. 7 shows a status of the analyzer system where the second window generated by the remote application program RA1 has been selected as the active window 142. Thus the second window provided by the remote application program RA1 is positioned on the top of the stack 154. The other second windows provided by the remote application programs RA2 to RAN and the first window generated by the data manager application program 130 are located below the active window 142.

For selection of another one of the windows to become the active window such as the nth second window, the user moves the cursor 156 onto the window 144.n that contains the screen shot SSn of the nth second window as illustrated in FIG. 7. When the user performs a mouse click on the window 144.n the windows of the stack 154 are rearranged such that the selected nth second window is moved to the top of the stack. Depending on the implementation the former active window can be moved to the position in the stack where the new active window was previously located as illustrated in FIG. 7 or to another stack position such as to the bottom of the stack.

Figure 8:
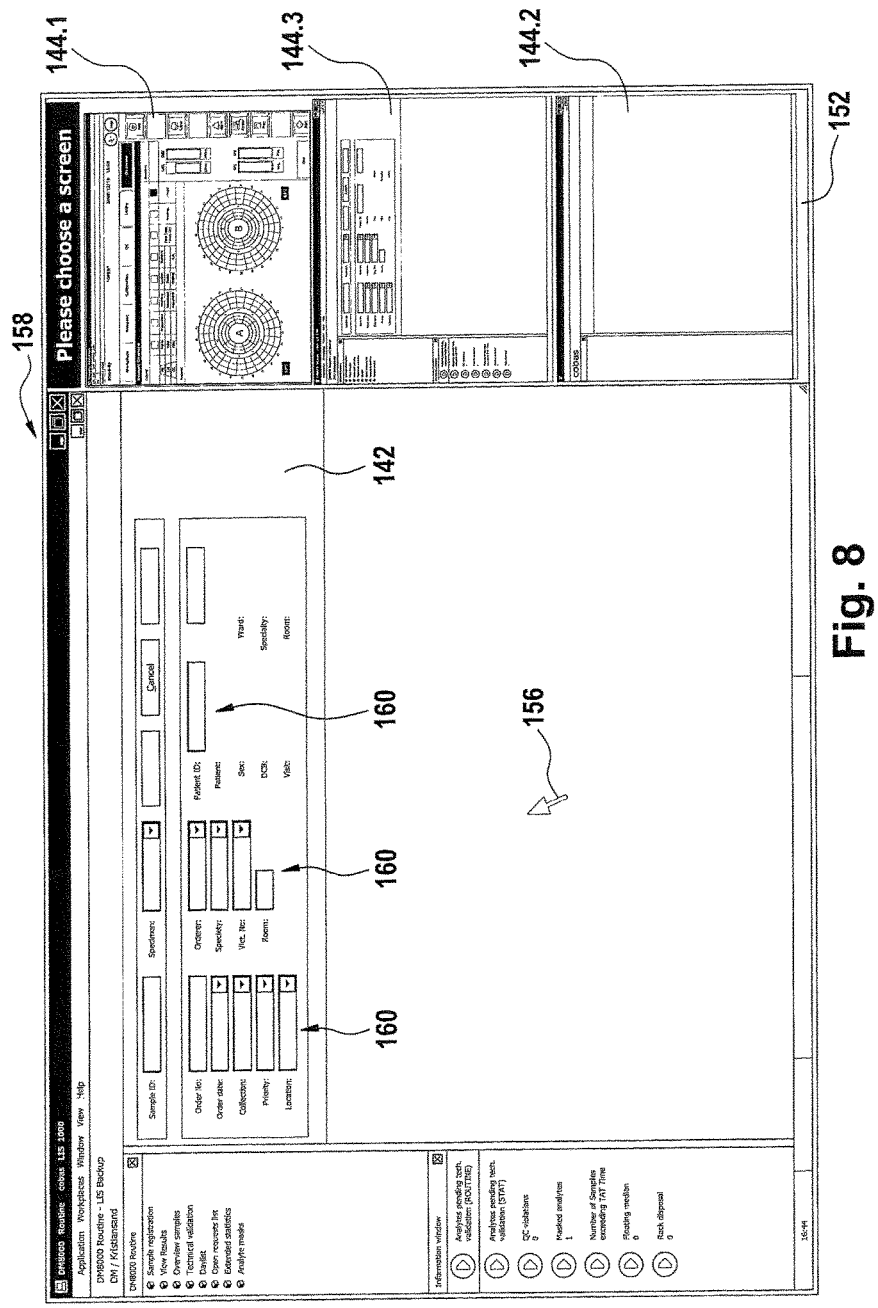
FIG. 8 depicts an embodiment of the screen image shown on the remote computer.

FIG. 8 shows a screen image 158 displayed on the monitor 138 of the remote computer 106 (cf. embodiment of FIG. 2). As shown in FIG. 8 the analysis system is in a status where the first window that is generated by the data manager application program 130 has been selected to be the active window 142 such that the user can enter data into the various data entry fields 160 contained in the first window. Data entry into the second windows is not possible, because the second windows are positioned below the topmost active window 142 such that it is not possible to move the cursor 156 onto these other windows of the stack 154 (cf. FIG. 7).

The side bar 152 contains windows 144.1 and 144.2 in addition to the window 144.3 that contains the screen shot of the first window. The windows 144.1 and 144.2 contain screen shots of two different automatic instruments that are coupled to the remote computer 106 in the embodiment considered here.

Figure 9:
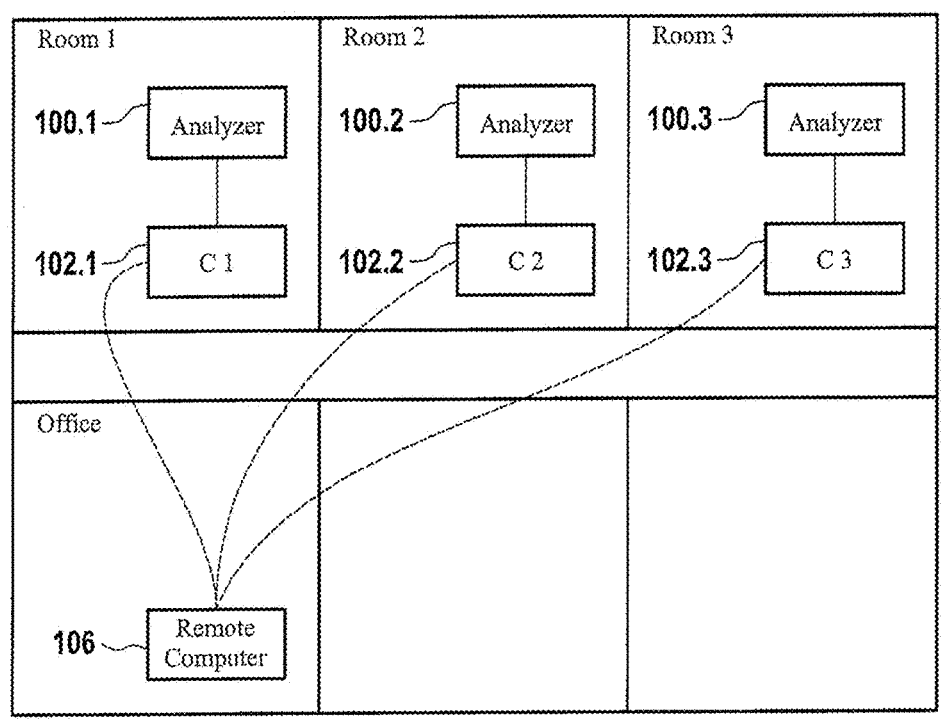
FIG. 9 depicts a diagram illustrating a further embodiment of an analysis system of the invention.

FIG. 9 shows the floor plan of a laboratory that comprises rooms 1, 2 and 3 and an office. An analyzer with a respective computer is located in each one of the rooms 1, 2 and 3 whereas the remote computer 106 is located in the office of the laboratory as shown in FIG. 9. Via the network 108 the remote computer 106 can establish communication channels to each one of the analyzer control computers C1, C2 and C3. This allows to remotely monitor and control the automatic analyzers from an operator that is located in the office of the laboratory.

Figure 10:
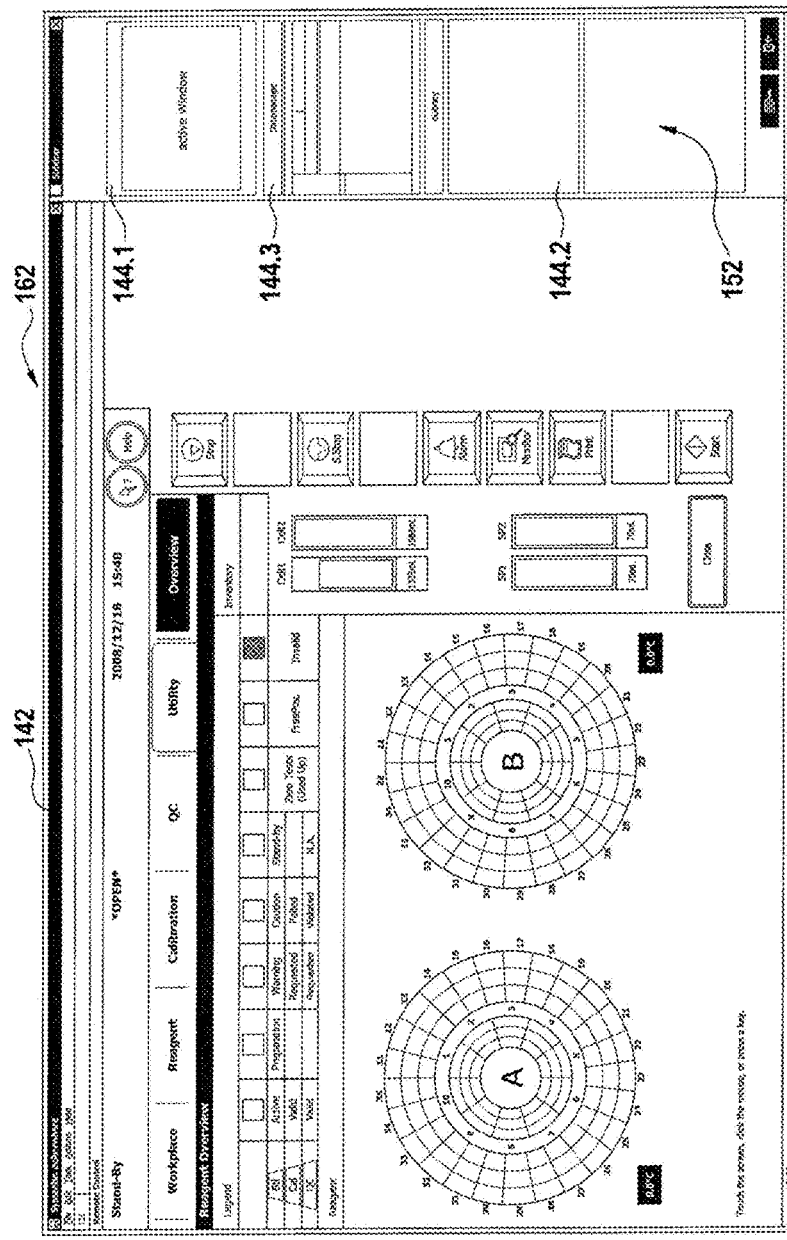
FIG. 10 depicts a further embodiment of the screen image shown on the remote computer.

FIG. 10 shows an alternative screen image 162 displayed on the monitor 138 of the remote computer 106 (cf. embodiment of FIG. 2). As shown in FIG. 10 the analysis system is in a status where the second window that is generated by the remote application program 124.1 (cf. FIG. 2) has been selected by the user to be the active window 142.

The sidebar 152 shows a window 144.1 that does not contain a screenshot of the second window that has been generated by the remote application program 124.1 but merely an indication that this window is the 'active window'. The other windows that have not been selected to be the active window 142 are shown as screenshots in the windows 144.2 and 144.3 in the sidebar 152.

Figure 11:
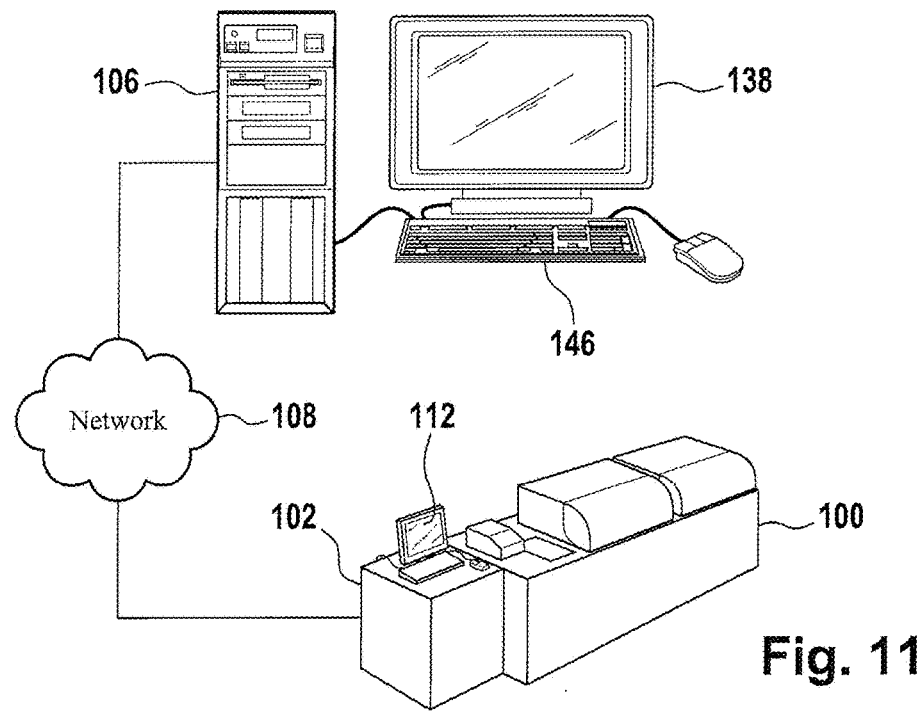
FIG. 11 depicts a picture of a further embodiment of an analysis system of the invention.

FIG. 11 shows an image of an embodiment of the analysis system of FIG. 1. Both the remote computer 106 and the analyzer control computer 102 can be implemented on the basis of standard personal computers running an operating system with a graphical user interface including windows.

Figure 12:
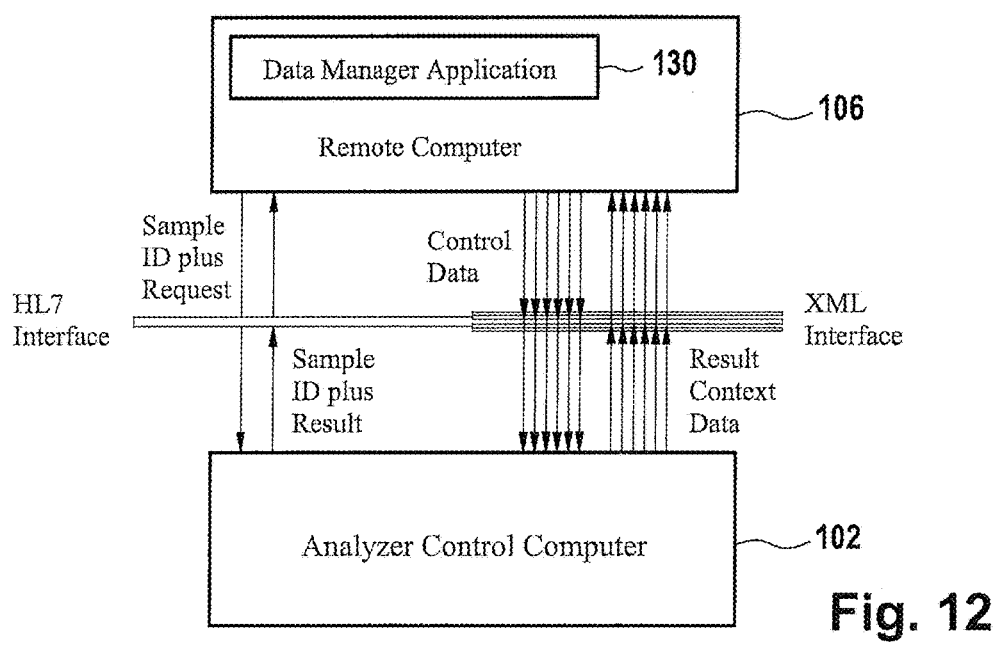
FIG. 12 depicts a block diagram showing a further embodiment of an analysis system of the invention.

FIG. 12 shows a further embodiment of an analysis system of the invention that implements first and second interfaces on the basis of a common physical layer provided by the network 108 (cf. FIG. 1 and FIG. 11). The analysis system may implement an HL7 interface and an XML interface for transmission of data between the data manager application program of the remote computer 106 and the analyzer control computer 102. The HL7 interface can be used for transmitting a request including a sample identifier from the data manager application program 130 that is executed by the remote computer 106 to the analyzer control computer 102 and for transmitting a portion of the analytical data being descriptive of the result obtained from the performance of the analysis and the sample identifier back to the data manager application program 130.

The request that is transmitted using the HL7 interface may be supplemented by additional control data that is transmitted from the data manager application program 130 to the analyzer control computer 102 by means of an XML document. Likewise the result data that is transmitted via the HL7 interface can be supplemented by an XML document containing result context data. The XML document containing the result context data is transmitted from the analyzer control computer 102 to the data manager application program 130 that is executed by the remote computer 106 in parallel or consecutive to the transmission of the result data via the HL7 interface. The communication via the HL7 interface and the exchange of the XML documents may be synchronous or asynchronous.

FIG. 13 shows a further embodiment of an analysis system of the invention. In the embodiment considered here the data manager application program 130 includes various functional components such as for configuration purposes, quality control data management, alarm/messages processing, communication with an external computer 164, such as cobas link, order entry processing, work list/sample status processing, workflow scheduling, communication with an external computer or computer network 166, such as a laboratory information system (LIS) and/or a hospital information system (HIS), result review processing, instrument overview processing, online help and printout processing.

The analyzer control application program 104 includes functional modules for system status handling, a module for providing the user interface on the monitor 112 (cf. FIGS. 1 and 11), rack with orders scheduling, service and maintenance, inventory control, sample processing, calibration data management, quality control (QC) sample processing, printout processing, online help, utility system setting and communications with the data manager application program such as via the HL7 interface and/or the XML interface (cf. FIG. 12).

The analyzer 100 itself also includes various control functionalities such as mechanical units control, data calculation, sequence scheduling, rack transportation, error handling and barcode/RFID reader control.

Obviously many modifications and variations of above disclosed embodiments of the present invention are possible in light of the above description. It is therefore to be understood, that within the scope of appended claims, the various embodiments of the invention may be practiced otherwise than as specifically devised.

What is claimed is:
1. An analysis system for analyzing biological samples comprising:
   a network;
   an automatic analyzer that induces a reaction of a biological sample with a reagent in accordance with control data that specifies or enables a requested action of the automatic analyzer, specifies the biological sample to be analyzed, and specifies a kind of analysis to be performed on the biological sample;
   a respective analyzer control computer communicatively coupled to the network and the automatic analyzer, and having an operating system configured to execute thereon:
      an analyzer control application program which is configured to:
         receive the control data via the network,
         generate one or more commands for execution by the automatic analyzer based on the control data received over the network, and
         generate a host screen image that renders under the control of the operating system, wherein the host screen image comprises up-to-date status information of the automatic analyzer, and
      a host application program configured to receive image data over the network and enter user data from the image data which interacts with the automatic analyzer into the analyzer control application program;
   a remote computer coupled communicatively via the network to the analyzer control computer, and having an input unit, a monitor and an operating system configured to execute thereon:
      a data manager application program configured to:
         send the control data to the analyzer control computer via the network, and
         generate a first window that requests a performance of the analysis of the biological sample by the analyzer, and
      a remote application program configured to:
         interoperate via the network with the host application program,
         generate a second window containing a duplicate of the host screen image generated by the analyzer control application program,
         transform into the image data the user data entered in the second window by the user via the input unit, and
         communicate the image data over the network to the host application program, and
      a user interface program which executes only on the remote computer and which is configured to:
         generate screen shots via an included screen shot component,
         display on the monitor at least a first display window and a second display window, the first display window being one of the first and second windows and the second display window containing a screen shot of the other one of the first and second windows, wherein only the first display window permits entry of the user data via the input unit,
         update repeatedly the screen shot via a screen shot update operation performed by the screen shot component, and
         receive via the input unit a user's selection of the first or the second window to display as the first display window on the monitor, wherein upon entry of a selection of the second window to become the first display window the user interface program of the remote computer is configured to: generate the screen shot of the first display window displayed on the monitor via the screen shot component, position the screen shot of the first display window as a new second window displayed on the monitor, display the selected second window as a new first window on the monitor to enable entry of the user data via the input unit, and communicate with the analyzer control application program without going through the data manager application program.

2. The analysis system of claim 1, wherein a time interval between two consecutive screen shot update operations is below five seconds.

3. The analysis system of claim 1, wherein a time interval between two consecutive screen shot update operations is below one second.

4. The analysis system of claim 1, wherein the user interface program has a window positioning component which positions in a stack the first window and the second window generated such that a user interaction is only enabled with the topmost window of the stack.

5. The analysis system of claim 4, wherein the windows of the stack have identical size and format.

6. The analysis system of claim 4, wherein the window positioning component changes the order of the stack in response to entry of the user's selection, such that the selected window becomes the topmost window of the stack.

7. The analysis system of claim 4, wherein the windows of the stack are aligned in a vertical direction such that only the topmost window is visible.

8. The analysis system of claim 4, wherein the second display window displays each screen shot generated.

9. The analysis system of claim 8, wherein the second display window shows each screen shot generated arranged in a side bar next to the first display window.

10. The analysis system of claim 1, wherein the first interface is a HL7 interface and the second interface is an XML interface.

11. The analysis system of claim 1, wherein a sample identifier is included in the first portion of the control data sent via the first interface by the remote computer, wherein the kind of analysis to be performed on the biological sample is included in the second portion of the control sent via the second interface, and wherein the first interface is a different interface from the second interface.

12. The analysis system of claim 1, wherein a sample identifier is included in the first portion of the control data sent via the first interface by the remote computer, wherein the first interface is a different interface from the second interface, and wherein the analytical data sent by the analyzer control computer includes the sample identifier sent back via the first interface.

13. The analysis system of claim 1, wherein a portion of the analytical data sent by analyzer control computer is result data transmitted via the first interface, and wherein the first interface is a different interface from the second interface.

14. The analysis system of claim 1, wherein a portion of the analytical data sent by analyzer control computer is context data transmitted via the second interface, and wherein the first interface is a different interface from the second interface.

15. The analysis system of claim 1, wherein a sample identifier is included in the first portion of the control data sent via the first interface by the remote computer, wherein the kind of analysis to be performed on the biological sample is included in the second portion of the control sent via the second interface, wherein the first interface is a different interface from the second interface, wherein a portion of the analytical data sent by analyzer control computer includes result data and the sample identifier transmitted via the first interface, and wherein another portion of the analytical data sent by analyzer control computer includes context data transmitted via the second interface.

16. A data processing method implemented by an analysis system for analyzing biological samples, in which the system comprises;
a network;
an automatic analyzer that induces a reaction of a biological sample with a reagent in accordance with control data that specifies or enables a requested action of the automatic analyzer, specifies the biological sample to be analyzed, and specifies a kind of analysis to be performed on the biological sample;
a respective analyzer control computer communicatively coupled to the network and the automatic analyzer, and having an operating system configured to execute thereon:
an analyzer control application program which is configured to:
receive the control data via the network,
generate one or more commands for execution by the automatic analyzer based on the control data received over the network, and
generate a host screen image that renders under the control of the operating system, wherein the host screen image comprises up-to-date status information of the automatic analyzer, and
a host application program configured to receive image data over the network and enter user data from the image data which interacts with the automatic analyzer into the analyzer control application program;
a remote computer coupled communicatively via the network to the analyzer control computer, and having an input unit, a monitor and an operating system configured to execute thereon:
a data manager application program configured to:
send the control data to the analyzer control computer via the network, and
generate a first window that requests a performance of the analysis of the biological sample by the analyzer, and
a remote application program configured to:
interoperate via the network with the host application program,
generate a second window containing a duplicate of the host screen image generated by the analyzer control application program,
transform into the image data the user data entered in the second window by the user via the input unit, and
communicate the image data over the network to the host application program, and
a user interface program which executes only on the remote computer and which is configured to:
generate screen shots via an included screen shot component,
display on the monitor at least a first display window and a second display window, the first display window being one of the first and second windows and the second display window containing a screen shot of the other one of the first and second windows, wherein only the first display window permits entry of the user data via the input unit,
update repeatedly the screen shot via a screen shot update operation performed by the screen shot component, and
receive via the input unit a user's selection of the first or the second window to display as the first display window on the monitor, wherein upon entry of a selection of the second window to become the first display window the user interface
program of the remote computer is configured to:
generate the screen shot of the first display window displayed on the monitor via the screen shot component, position the screen shot of the first display window as a new second window displayed on the monitor,
display the selected second window as a new first window on the monitor to enable entry of the user data via the input unit, and
communicate with the analyzer control application program without going through the data manager application program, the method comprising:

generating the host screen image by the analyzer control application program of the respective analyzer control computer, wherein the host screen image comprises the up-to-date status information of the automatic analyzer communicatively coupled thereto and one or more data entry fields for entry of the control data;

generating the first window by the data manager application program;

generating the second window by the remote application program of the remote computer;

receiving a user's selection of the first window or the second windows for displaying as the first display window, displaying and positioning on the monitor, via the user interface program, the first display window of the selected one of the first and second windows and the second display window containing the screen shot generated by the screen shot component of the user interface program of the other, non-selected one of the first and second windows, wherein each second display window displayed on the monitor is positioned in a stack such that a user interaction is only enabled with a topmost second display window of the stack;

transforming data entered by the user in the first display window into image data by the remote application program; and communicating over the network, without going through the data manager application program, the image data to the host application program which then enters the data entered by the user from the image data into the analyzer control application program of the respective analyzer control computer.

17. The method of claim 16, further comprising directly interacting via the host screen image with the analyzer control application program.

18. The method of claim 16, in which the analysis system for analyzing biological samples further comprises:

a first interface operable to transmit a sample identifier and a request for performing an analysis of the sample from the remote computer to the respective analyzer control computer and to transmit the sample identifier and a result of the analysis in response to the request from the respective analyzer control computer to the remote computer, and a second interface operable to transmit at least a portion of the control data from the remote computer to the respective analyzer control computer and to transmit at least a portion of the result context data related to the requested analysis from the respective analyzer control computer to the remote computer, the method further comprising:

receiving the user's entry of the control data via the first display window, transmitting via the first interface a sample identifier and a request for performing an analysis of the sample, the request being specified by data entered by the user into the first window displayed as the first display window, and transmitting via the second interface the at least one portion of the control data being transmitted from the remote computer to the respective analyzer control computer that has generated the second window in response to the user's entry of the control data.

19. The method of claim 18, further comprising:

analyzing the biological sample by the analyzer that is coupled to the respective analyzer control computer that generated the second window in response to the user's entry of the control data, and receiving via the first interface the analytical data resulting from the analysis of the biological sample, and receiving via the second interface the at least a portion of the result context data related to the requested analysis and the sample identifier by the remote computer.

* * * * *

UNITED STATES PATENT AND TRADEMARK OFFICE
CERTIFICATE OF CORRECTION

PATENT NO. : 10,248,373 B2
APPLICATION NO. : 15/018006
DATED : April 2, 2019
INVENTOR(S) : Marco Maetzler and Juergen Wiemer Page 1 of 1

It is certified that error appears in the above-identified patent and that said Letters Patent is hereby corrected as shown below:

In the Claims

In Column 18, Claim 16, Lines 37-38, after "by the", insert --at least one--.

Signed and Sealed this
Twelfth Day of November, 2019

Andrei Iancu
*Director of the United States Patent and Trademark Office*